United States Patent [19]

Carroll et al.

[11] Patent Number: 5,197,017
[45] Date of Patent: Mar. 23, 1993

[54] POTENTIOPHOTOMETRIC FIBRINOGEN DETERMINATION

[76] Inventors: Wallace E. Carroll; R. David Jackson, both of 1556 San Leandro La., Santa Barbara County, Santa Barbara, Calif. 93108

[21] Appl. No.: 589,317

[22] Filed: Sep. 27, 1990

[51] Int. Cl.$^5$ ............... G01N 33/86; C12Q 1/56
[52] U.S. Cl. ............... 364/497; 364/413.09; 435/13; 422/73; 436/69
[58] Field of Search ............... 364/413.07, 413.08, 364/413.09, 496, 558, 497, 499; 436/69; 435/13; 422/73

[56] References Cited

U.S. PATENT DOCUMENTS

| | | | |
|---|---|---|---|
| 3,307,392 | 3/1967 | Owen et al. | 73/64.1 |
| 3,458,287 | 7/1969 | Gross et al. | 436/69 |
| 3,593,568 | 7/1971 | Schmitz | 73/64.1 |
| 3,607,099 | 9/1971 | Scordato | 422/73 X |
| 3,905,769 | 9/1975 | Carroll et al. | 8/128.1 |
| 4,047,890 | 9/1977 | Eichelberger | 422/73 X |
| 4,217,107 | 8/1980 | Saito et al. | 422/73 X |
| 4,252,536 | 2/1981 | Kishimoto et al. | 422/73 X |
| 4,289,498 | 9/1981 | Baughman et al. | 436/69 X |
| 4,454,752 | 6/1984 | Scordato | 436/69 X |
| 4,720,787 | 1/1988 | Lipscomb | 364/413.07 |
| 4,766,083 | 8/1988 | Miyashita et al. | 436/517 |
| 4,884,213 | 11/1989 | Iwata et al. | 364/497 |
| 4,959,796 | 9/1990 | Hidaka et al. | 364/497 |

OTHER PUBLICATIONS

Carroll W. E., Jackson R. D., & Wilcox A. A., "Potentiophotometry", *Research Communications Chemical Pathology and Pharmacology;* vol. 14, No. 2 (1976) pp. 387-390.

Carroll W. E., Jackson R. D., & Wilcox A. A., "Application of a New Instrument, the Potentiometer", *Clinical Chemistry;* vol. 24, No. 1 (1978) pp. 92-94.

Carroll W. E., Jackson R. D., & Wilcox A. A., "Potentiophotometry," *Am. J. Clin. Path.;* vol. 70, No. 2 (1978) pp. 322-323.

Carroll W. E., Jackson, R. D., and Wilcox A. A., "Potentiophotometric Platelet Aggregation", *Journal of Clinical Engineering;* vol. 4, No. 2 (1979) pp. 171-173.

Clauss A. "Gerinnungsphysiologische Schnellmethode zur Bestimmung des Fibrinogens", *Acta Haematol* 17; (1957) pp. 237-246 (no translation).

Dunikoski L. K. Jr., Guenther R., Grohs H. K., Calvert K. M., Harris A. L., "An Evaluation of the Fibrinogen Method and Calibration for the duPont aca", publication from duPont, Dec. 1981.

(List continued on next page.)

*Primary Examiner*—Parshotam S. Lall
*Assistant Examiner*—Collin W. Park
*Attorney, Agent, or Firm*—John F. A. Earley; John F. A. Earley, III

[57] ABSTRACT

The fibrinogen concentration of a blood plasma sample is measured and simultaneously the prothrombin time is determined. Potentiophotometric apparatus is used in which the output signal is applied to an analog/digital converter and digital recorder. Digital voltage values are developed and then printed in an array. A computer records digital voltage values produced by the apparatus with a plasma sample in the test tube before injection of thromboplastin. The time of the injection is identified by a substantial change in the recorded voltage values. After a short time delay the digital voltage value is noted and thereafter this voltage value is compared with a second voltage value. A difference of three or more identifies the beginning of clotting. The first of the two voltage numbers is identified x and is compared with the voltage value 60 seconds later, which is identified y. The delta voltage value is y−x. The delta voltage values for two samples of known but different fibrinogen concentrations, one high and one low, are plotted on a linear calibration curve drawn, which is used to determine the fibrinogen concentration values of plasma samples having unknown fibrinogen concentration.

26 Claims, 8 Drawing Sheets

OTHER PUBLICATIONS

Losner S., Volk B. W., Jacobi N., & Newhouse S., "Spectrophotometric Studies on Clot Density", *J. Clin. Med.;* vol. 38 (1951) pp. 28–38.

"Factor Assays: Fibrinogen" in Triplett D. A., Harms C. S., *Procedures for the Coagulation Laboratory,* (Educational Products Division), American Society of Clinical Pathologists, 1981 pp. 23–26.

Cawley, L. P., and Eberhardt, L. "A Permanent Record for Determinations of Prothrombin Time, Using the Spinco Analystrol as a Recorder," *The American Journal of Clinical Pathology,* vol. 37, No. 2 (1962) pp. 219–226.

Woody, G. L., Brenner, N. & Foster R. L., "A Comparison Study of 175 Duplicate Determinations Using the Electra 500 and the Standard Fibrometers," *Technical Bulletin of the Registry of Medical Technologists,* vol. 39, No. 12 (1970) pp. 112–115.

Scordato, E. A. "Principles of Photometric Clot Detection," *Analytical Instrumentation Exhibit,* Paris, 1970.

Carroll, W. E. "Potentiophotometry: A Multi-Purpose Instrument for Chemistry and Hematology; An Electrical Solution to Beer's Law," *American Society of Clinical Pathologists Exhibit,* Dallas (1978).

POTENTIOPHOTOMETRIC FIBRINOGEN DETERMINATION

BACKGROUND

The present application relates to U.S. Pat. No. 3,905,769 dated Sep. 16, 1975, issued to Wallace E. Carroll and Richard D. Jackson. The present application describes a variation of, or an improvement over, the method and apparatus shown and described in that earlier patent.

SUMMARY OF THE INVENTION

The invention relates broadly to an improved method of measuring the optical density (O.D.) of a fluid sample, particularly blood plasma. The invention provides a method of, and apparatus for, developing digital electrical signals representing voltage values which are linearly related to the optical density (O.D.) of a semitransparent fluid aliquot of citrated human plasma using a potentiophotometer. Since the optical density of the plasma is directly proportional to fibrinogen concentration, the method and apparatus of the present invention measures fibrinogen concentration. As is well known, fibrinogen is a plasma protein manufactured by the liver and is essential to the clotting of blood.

The method and apparatus of the present invention is also used to measure prothrombin time simultaneously. As is also well known, prothrombin is one of several clotting factors manufactured in the liver, and prothrombin time is the time between the injection of a reagent into the plasma and the beginning of formation of a clot. The prothrombin time test indicates the level of prothrombin in the blood plasma sample and is a measure of the coagulation response. The apparatus may also be used to measure other clotting times such as the partial thromboplastin time or thrombin time.

BRIEF DESCRIPTION OF THE DRAWINGS

FIGS. 2, 3, 4, and 5 show pertinent portions of arrays of numbers representing recording of digital voltage outputs from the A/D converter and digital recorder.

DETAILED DESCRIPTION OF THE DRAWINGS

Figure 1:
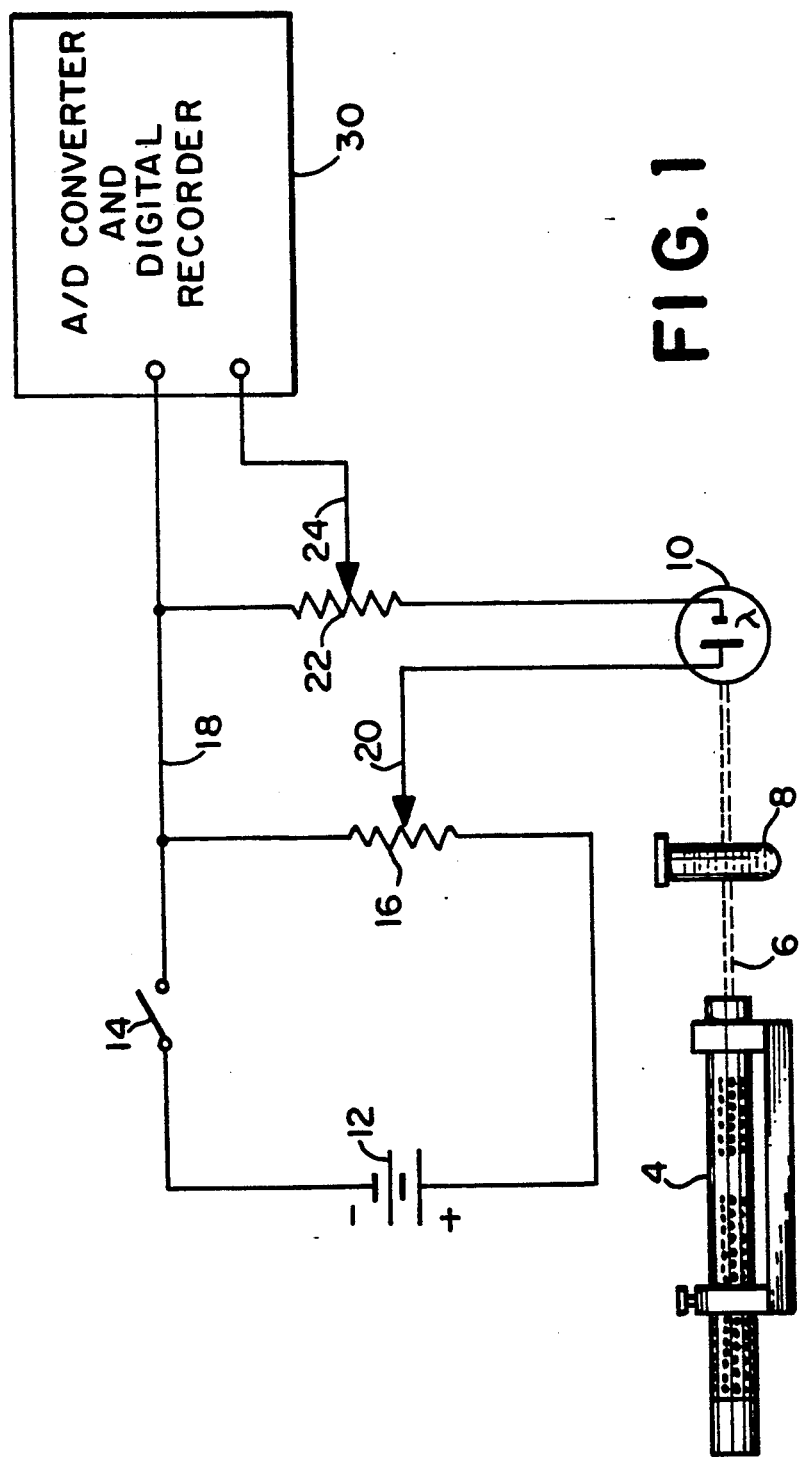
FIG. 1 is a diagram of potentiophotometric (hereinafter sometimes "POTENS") fibrinogen determination apparatus generally similar to that shown in FIG. 1 of U.S. Pat. No. 3,905,769 but differing in that the output of the network is applied to an analog/digital (A/D) converter and recording device.

Referring now to FIG. 1, there is shown a light source 4 which may be a low power gas laser producing a beam of light 6 which passes through a sample test tube or cuvette 8 and is received by detection means 10 which is preferably a silicon or selenium generating photocell (photovoltaic cell). Battery 12 acts as a constant voltage DC source. Its negative terminal is connected through switch 14 to one end of variable resistor 16 and its positive terminal is connected directly to the opposite end of variable resistor 16. The combination of battery 12 and variable resistor 16 provides a variable DC voltage source, the variable voltage being derivable between line 18 at the upper terminal of resistor 16 and wiper 20. This variable DC voltage source is connected in series with detection means 10, the positive output of detection means 10 being connected to the wiper 20 of variable resistor 16 so that the voltage produced by the variable voltage DC source opposes the voltage produced by the detection means. The negative output of detection means 10 is connected through variable resistor 22 to line 18. Thus, the voltage across variable resistor 22 is the difference between the voltage produced by the variable voltage DC source and the voltage produced by the photovoltaic cell. The output of the electrical network is taken between line 18 and wiper 24 of variable resistor 22. Thus, variable resistor 22 acts as a multiplier, multiplying the voltage produced as a result of the aforesaid subtraction by a selective variable depending on the setting of variable resistor 22. The potentiophotometer just described embodies the electrical-analog solution to Beer's Law and its output is expressed directly in the concentration of the substance being measured.

In the present invention, wiper 24 is placed at a position to give a suitable output and is not varied during the running of the test. The output between line 18 and wiper 24 is delivered to an A/D converter and digital recorder 30. The equipment 30 is known and may, for example, be a device sold commercially as ADALAB-PC and ADAPT available from Interactive Microware, Inc., State College, Pennsylvania. The signal across variable resistor 22 is an analog signal and hence the portion of the signal between leads 18 and wiper 24, which is applied to the A/D converter and digital recorder 30, is also analog.

Aliquots of citrated plasma specimens from hospitalized patients were obtained and used. Some of the plasmas were also diluted 1:4 with Owren's Veronal Buffer (pH 7.35) before analysis. Kabi Vitrum lyophilized powder human fibrinogen (having 1.0 Gm (gram) of 90 percent clottable fibrinogen, sodium citrate 1.0 Gm and sodium chloride 0.4 Gm) was dissolved in 100 ml (milliliters) of distilled water to give the stock fibrinogen solution. Dilutions of 1:2 and 1:32 of this stock fibrinogen were freshly prepared, using as dilutent 10.0 Gm sodium citrate and 4.0 Gm sodium chloride per liter (L), to give dilutions for high and low fibrinogen standards. To prepare the working high and low fibrinogen standards, each of the above fibrinogen solutions was mixed 1:2 with fresh citrated human plasma having an average value of 2.40 Gm/L. This plasma supplied all other clotting factors. Since the fibrinogen in the stock solution is 90 percent clottable, its 1:2 dilution has a concentration of 4.50 Gm/L of clottable fibrinogen. A 1:2 dilution of this with the 2.40 Gm/L fresh plasma gives a high working fibrinogen standard of 3.45 Gm/L. By similar arithmetic, the low working fibrinogen standard value is 1.33 Gm/L. In carrying out the method of the present invention, 0.2 ml of Thromboplastin C were added to 0.1 ml of the citrated plasma in the 37° C. regulated potentiophotometer.

As clotting of the sample in test tube 8 occurs, the A/D converter counts and produces a digital value of voltage every 0.05 seconds. These values are stored and then printed by the recorder as an array of numbers, the printing being from left to right and line by line, top to bottom. There are twenty numbers representing voltage values in each line. Hence, one line represents one second in time (20×0.05 seconds). Individual numbers in the same column are twenty sequential numbers apart. Hence, the time difference between two adjacent numbers in a column is one second.

The A/D converter and digital recorder 30 is used with an IBM compatible computer which is programmed as follows:

(a) with citrated blood plasma such as described above in the test tube 8, the equipment 30 sequentially records voltage values for a few seconds before injection of thromboplastin. As is known, thromboplastin is one of the factors in the human body that causes blood to clot. Prothrombin is another. Fibrinogen is yet another. When thromboplastin is injected into test tube 8, it combines with the prothrombin and calcium in the blood plasma sample to form thrombin. The thrombin then converts the fibrinogen to the fibrous substance fibrin that allows clot formation.

Figure 2:
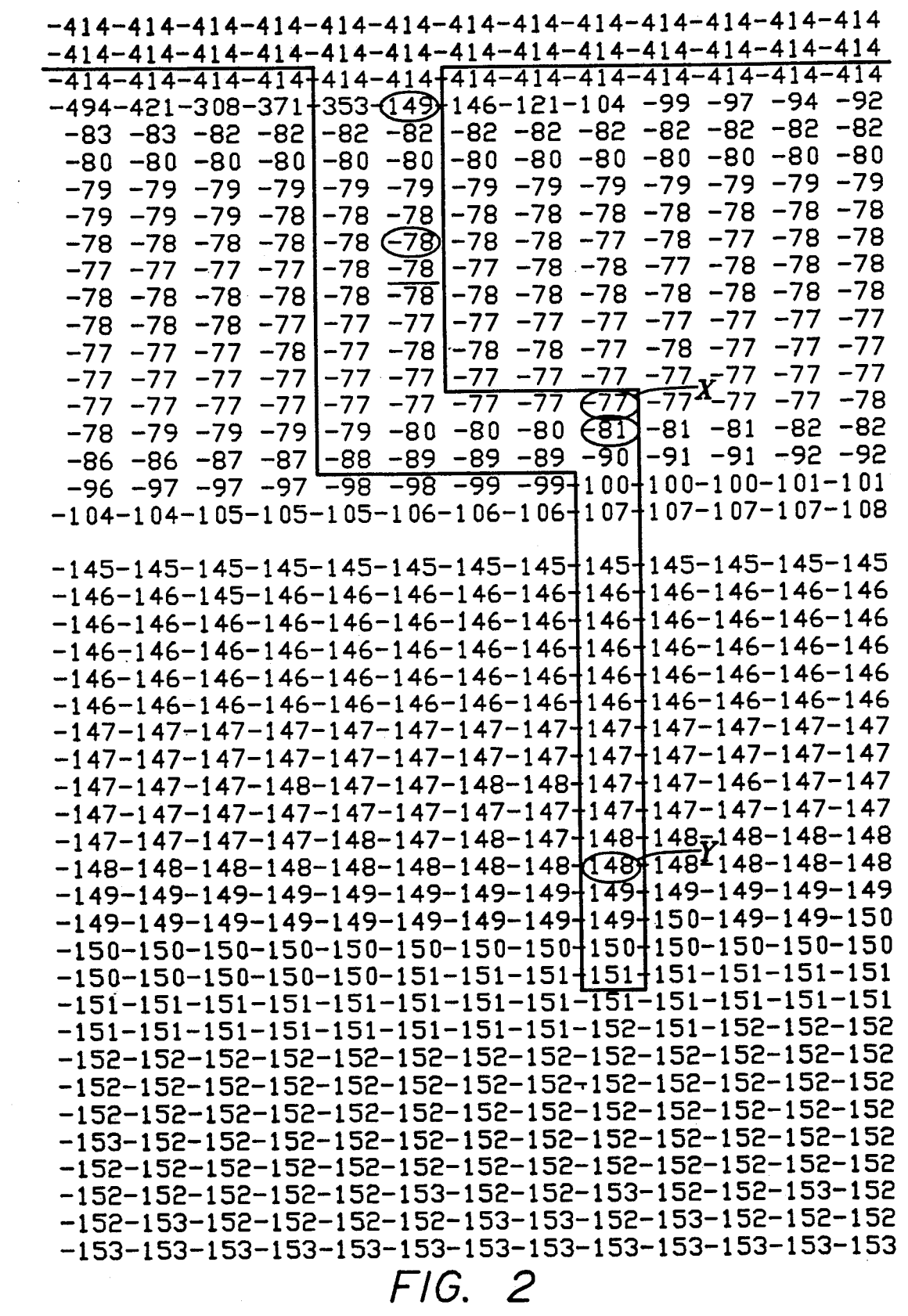

Before injection of the thromboplastin, the output from the A/D converter is constant. When thromboplastin is injected into the blood plasma in test tube 8, a significant change occurs in the recorded voltage values, of fifty or more, plus or minus. This change in the recorded values identifies the injection time. In FIG. 2 for example, a change from 353 to 149 is recorded at line 4, column 6.

(b) The computer then allows a short period of time, for example, six seconds, for the clearing up of any disturbance or turbulence caused by the injection. In FIG. 2, the voltage value six seconds after the injection is 78, recorded at line 10, column 6.

(c) Following the six second interval, the computer is programmed to look for a change greater than three in voltage values within a time period of one second. This will indicate the beginning of clotting. As previously indicated, adjacent numbers in a column are one second apart. In FIG. 2, a change greater than three in one second (from 77-81) occurs at lines 16-17, column 9. The beginning of this change is 6.2 seconds after the six second interval or 12.2 seconds after the injection of the thromboplastin. Thus, clotting started 12.2 seconds after the injection. The first of the two numbers (77) is identified as x. This marks the end of prothrombin time and the beginning of the fibrinogen determination. To give times which would conform to other clotting instruments which are not as sensitive and give longer prothrombin times, one or even two seconds could arbitrarily be added to the potentiophotometric prothrombin times. Because this would be done consistently, there would be no sacrifice of accuracy.

(d) Following the noting of a change greater than three in recorded voltage values within one second, the computer is programmed to allow sixty seconds to pass after point x. The voltage value is then read and identified as y. In FIG. 2, the y number is 148 which appears at line 76, column 9. This count represents the maximum absorbance level of the clotting specimen.

(e) The difference between the voltage values of y and x (y−x) is the delta. This is the difference between the maximum absorbance count of clotted plasma and the baseline count of unclotted plasma. This difference is directly proportional to optical density and also directly proportional to fibrinogen concentration. In FIG. 2, the delta value (y−x) is 148−77 or 71.

Figure 6:
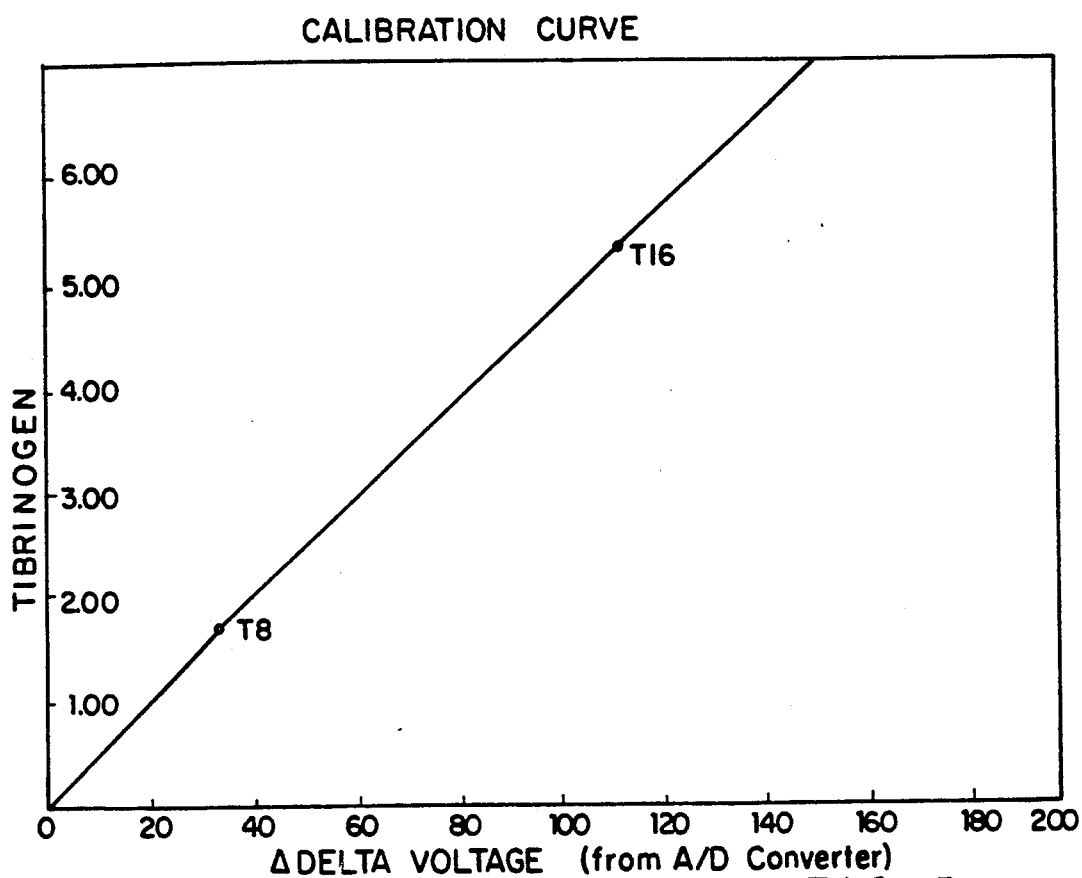
FIG. 6 is a calibration curve of fibrinogen concentration plotted against a difference or delta voltage developed from the voltage output of the A/D converter and digital recorder.

In carrying out the method of the present invention, two plasma samples of known but different fibrinogen concentration, one high and one low, are placed separately in the test tube 8 and separately tested to produce two arrays of digital voltage values. The method used is that just described in connection with FIG. 2. Assume that the sample used to produce the array (the pertinent portion of which is shown in FIG. 2) is known to have a high fibrinogen concentration of 3.45 Gm/L (Grams per liter). The delta value (71) is then marked as the first point on a calibration chart opposite the fibrinogen value of 3.45. This is shown in FIG. 6. In the chart of FIG. 6, delta voltage values are plotted against fibrinogen concentration (Gm/L).

Figure 3:
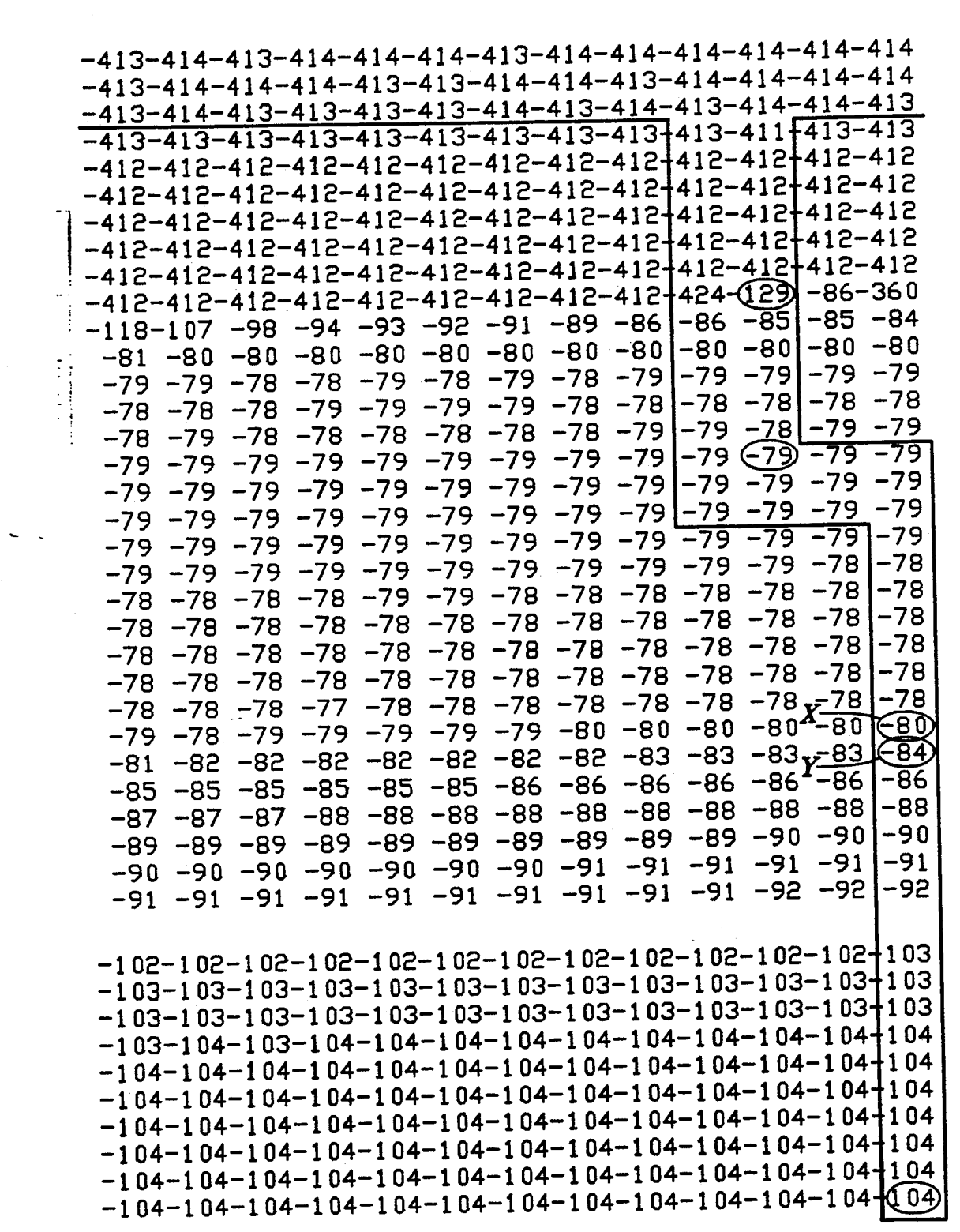

FIG. 3 represents pertinent portions of an array of voltage values produced when a second sample, known to have low fibrinogen concentration, is tested in test tube 8 using the method described herein before.

In the array of FIG. 3, thromboplastin is injected at line 10, column 10 (424−129). The beginning of clotting (80−84) occurs at line 26, column 12 or 16.1 seconds after injection. The x value is 80. The y value, developed sixty seconds later, is 104, and the delta (y−x) is 24 (104−80). The plasma sample is known to have a fibrinogen concentration of 1.33 Gm/L. Hence, the delta voltage value 24 is marked as a second point on the chart of FIG. 6 opposite the fibrinogen concentration value of 1.33.

The next step is to draw a straight line between the two delta values 71 and 24 developed above and to project the line linearly in both directions. This line is now a calibration "curve" which can be used to determine the fibrinogen concentration in samples of unknown fibrinogen concentration.

Figure 4:
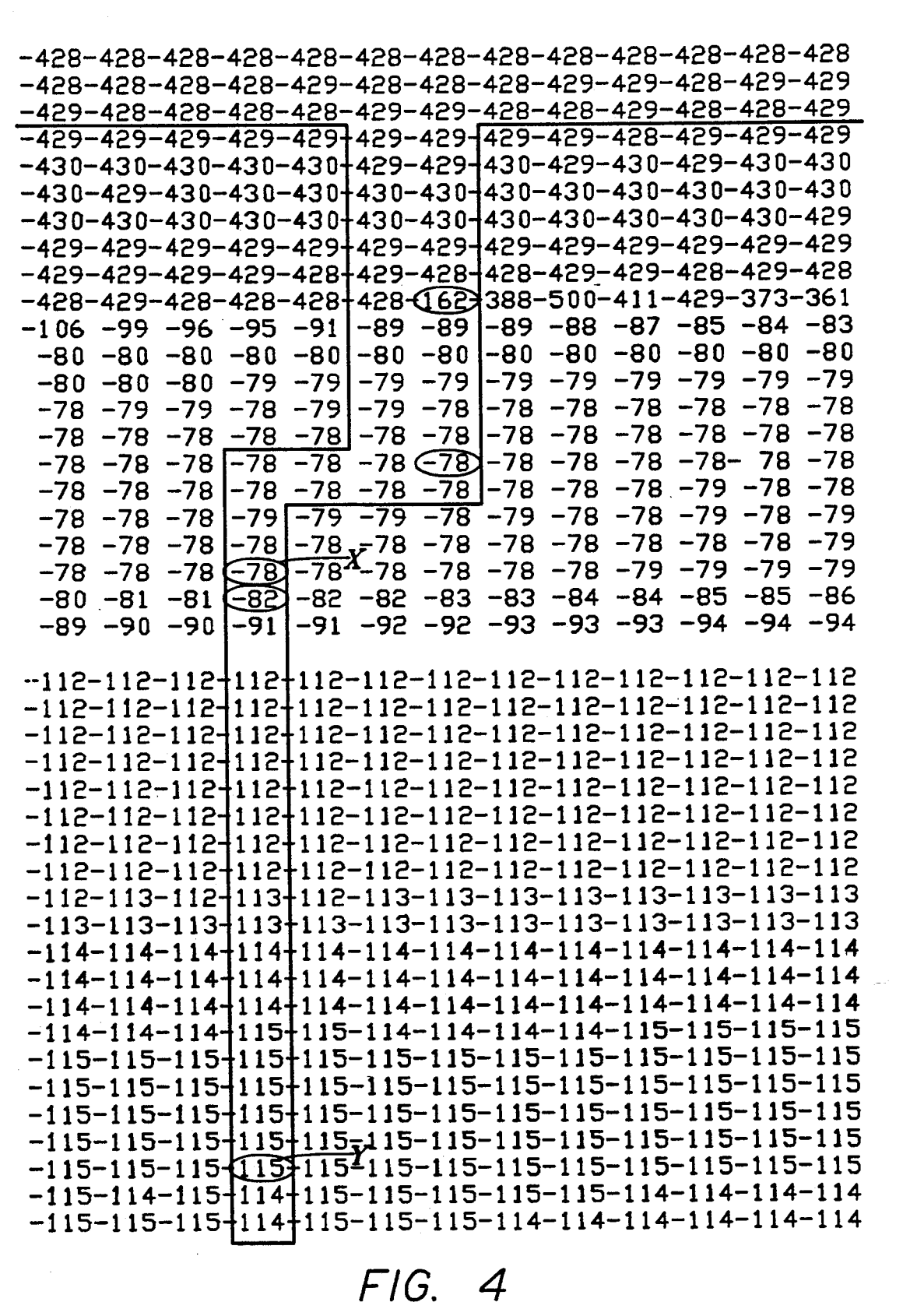
Figure 5:
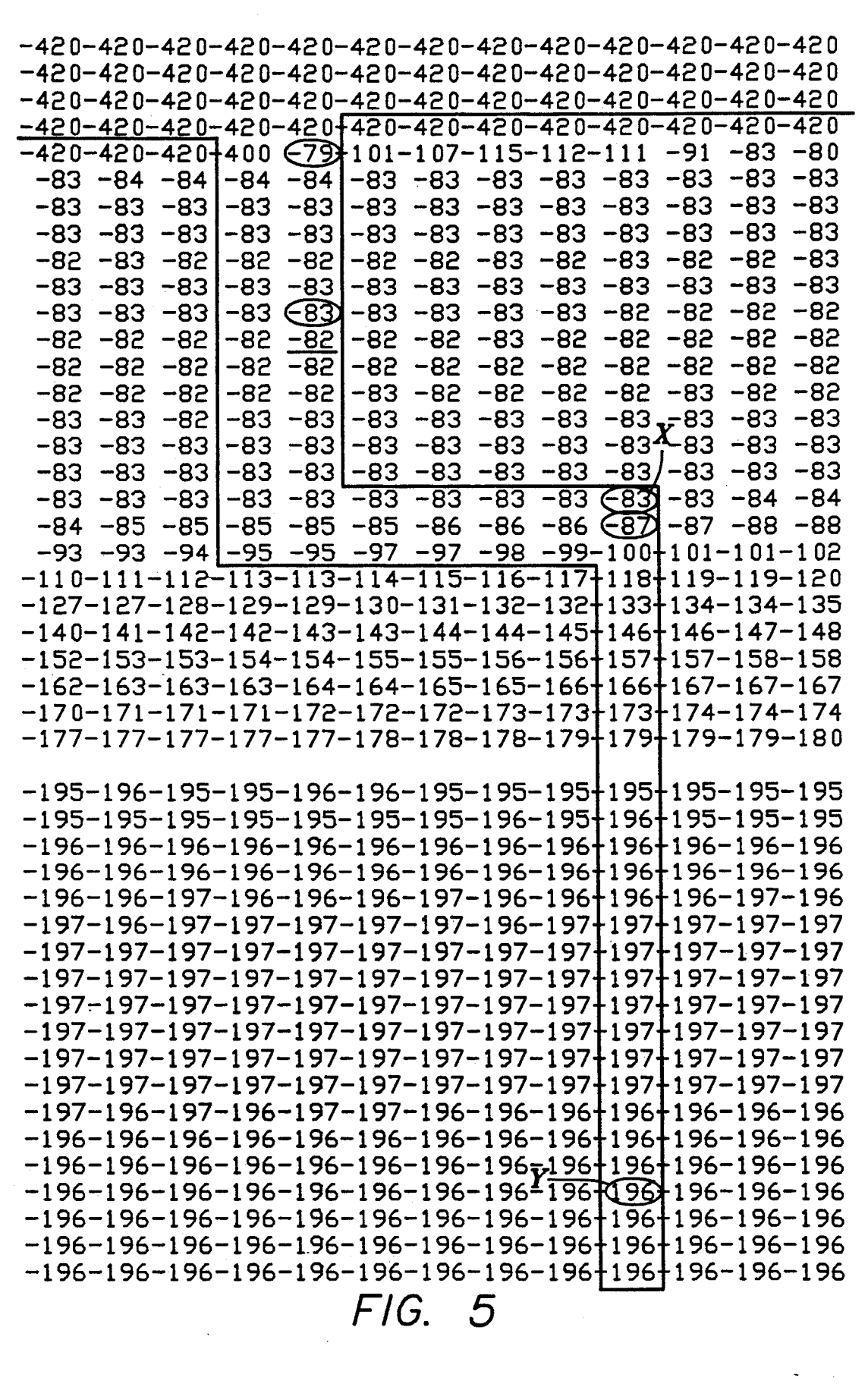

FIGS. 4 and 5 show pertinent portions of two arrays developed using the method and apparatus described in connection with FIGS. 2 and 3. However, the plasma samples placed in test tube 8 to develop the voltage arrays of FIGS. 4 and 5 have unknown fibrinogen concentration.

In FIG. 4, the x number developed by the method described for FIGS. 2 and 3 is 78 (line 20, column 4) and the y number developed sixty seconds later is 115. The delta (y−x) is 37. An examination of the calibration chart of FIG. 6 shows that a delta value of 37 corresponds to a fibrinogen concentration of 1.85. Thus, the unknown fibrinogen concentration of the sample in FIG. 4 is 1.85 Gm/L.

Similarly, in the array of FIG. 5, the x value developed at line 18, column 10 is 83, the y value developed sixty seconds later is 196, the delta value (y−x) is 113, and the unknown fibrinogen concentration of the sample as obtained from the calibration chart of FIG. 6 is 5.40 Gm/L. Instead of reading the values of unknown fibrinogen concentration from the curve in FIG. 6, the MATRIX computer could be used to calculate the unknown values from the formula $y = mx + b$, in which "m" is slope and "b" is intercept value or bias, both of which are discussed briefly later.

As indicated previously, the time at which the value x is developed identifies the beginning of clotting, and the time which elapses between the injection of thromboplastin and the time of x is the prothrombin time. In the array of FIG. 2, the injection of the thromboplastin into the high fibrinogen sample occurred at line 4, column 6. The value x was developed at line 16, column 9. Hence, the prothrombin time was 12.2 seconds. In the array of FIG. 3, the thromboplastin was injected at line 10, column 10 and the x value was developed at line 26, column 12 or 16.1 seconds after the injection. Since this marks the beginning of clotting, the prothrombin time for the low fibrinogen sample was 16.1 seconds (26.6−10.5). In FIG. 4, the injection was made at line 10, column 7 and the x value was developed at line 20, column 4 or 9.8 seconds after the injection. Thus, the prothrombin time was 9.8 seconds. In FIG. 5, the injection was made at line 5, column 5 and the x value was developed at line 18, column 10 or 13.3 seconds after the injection. Thus, the prothrombin time was 13.3 seconds.

It will be seen that the POTENS apparatus and method of the present application is useful not only in determining the fibrinogen concentration of unknown plasma samples or other liquid samples, but also in determining potentiophotometric prothrombin time simultaneously with the measurement of fibrinogen concentration.

It should be mentioned that after clotting begins, at time point x, the changes in optical density are initially linear but then begin to follow an exponential decay curve. By following the formula for the decay curve, we are able to project the end point y. Hence, by following the curve for only fifteen or twenty seconds we achieve the same fibrinogen concentration as for the sixty seconds mentioned in the foregoing description.

It should be noted that if the last array value is less than 60 seconds from time point x, then the largest value subsequent to x is considered to be y, and a notation is made that the fibrinogen value may be somewhat low.

The method of the present invention, using the potentiophotometer (POTENS) shown in FIG. 1, produced results which were compared with two other automated methods, one using a DuPont aca IV Analyzer and another using an MLA Electra 900 C Analyzer. The results were also compared with the Clauss manual method. Using the Clauss method as a reference, we found that the potentiophotometer method produced results having acceptable correlation coefficients, having a more advantageous slope (m=0.985), and having a smaller intercept value (b=0.08 Gm/L) than either the DuPont aca method or the MLA electric method.

The correlation coefficients (r obtained with each instrument were as follows: potentiophotometer, r=0.942; aca, r=0.979; and MLA(®), r=0.963, compared to the Clauss method. Since the accuracy of the Clauss method is only +/−10%, better correlation coefficients would not be anticipated. Slope (m), which reflects the correspondence of the value obtained by one method with that of another method, would have a value of 1.0 for perfect correspondence. The slope (m) for the POTENS (potentiophotometer) was m=0.986 and was more favorable than the m=0.889 for the aca, and definitely more favorable than the m=0.775 for the MLA(®). The intercept (b), which indicates the bias of a method, was also somewhat better for the potentiophotometer (b=0.08 Gm/L) than for the aca (b=0.21 Gm/L) or the MLA(®) (b=0.35 Gm/L). In any event, all of these statistical data correspond well to a comparison of the aca method to the Clauss method (Data Fi(®)) as published by duPont in a publication entitled "An Evaluation of the Fibrinogen Method and Calibration for the duPont aca," written by Dunikoski, Guenther, Grohs, Calvert and Harris (1981). Here, these analyses in two independent institutions had correlation coefficients of 0.96 and 0.95, slopes of 1.05 and 1.04, and intercepts of 0.016 Gm/L and 0.43 Gm/L, respectively. Statistical data, therefore, support clinical usefulness for the potentiophotometer and the method of using the potentiophotometer as described hereinabove.

Critical fibrinogen values for patients are in or below the 1.00 Gm/L range. Very few hospitalized patients have values this low. To obtain test samples in this low fibrinogen range, therefore, patient samples were diluted 1:4 with Owren's Veronal Buffer (pH 7.35). Since this is the buffer used to dilute the plasma samples in the Clauss method of fibrinogen determination, this buffer does not appear to denature the protein significantly, and therefore gave satisfactory low value specimens for the instruments to analyze in this study.

The Clauss manual method, referred to hereinabove, is described in a publication in German in an article by A. Clauss, Gerinnungsphysiologische Schnellmethode zur Bestimmung des Fibrinogens. Acta Haematol 1957; 17: 237-246. In connection with the development of the present invention, for comparison purposes, a modified Clauss method using Data-Fi(®) reagents was employed. One tenth of a milliliter of thrombin reagent (100 NIH units/ml) was added to 0.2 ml of citrated human plasma which had been diluted 1:10 with Owren's Veronal Buffer (pH 7.35) and incubated at 37° C., which is normal blood temperature. The clotting time which resulted was detected with the Mechrolab Clot Timer, commercially available from Heller Laboratories, Santa Rosa, Calif. Since the logarithm of the time required for the clot to form is inversely related to the logarithm of the fibrinogen concentration, the results could be determined with a calibration curve on log-log paper.

To summarize the potentiophotometric (POTENS) fibrinogen method of the present invention, 0.2 ml of Thromboplastin C were added to 0.1 ml of the citrated plasma in the 37° C. regulated potentiophotometer, whose output voltage was converted from an analog signal to a digital signal and counted every 0.05 seconds by the AD LAB-PC ™ card. After injection and a short delay, the output was initially constant so counts were the same. This was the baseline count; but, as clotting occurred, the counts changed. When the difference between counts changed a predetermined amount, the prothrombin time was indicated. Sixty seconds later, the count representing the maximum absorbance level of the clotted specimen was obtained. This maximum absorbance count minus the baseline count gave a count difference which was directly related to the fibrinogen concentration in that sample. Calibration was achieved with the high and low working fibrinogen standards. Net counts from the high standard and low standard defined the straight line calibration curve from which the net counts of the unknown plasmas were converted to the fibrinogen values for the unknowns. The arithmetic involved was performed by the MATRIX computer.

In the aca IV fibrinogen method for fibrinogen determination, 0.4 ml of citrated plasma were added to the duPont Fibrinogen Reagent Packet and the fibrinogen concentrations were determined automatically by the aca IV instrument.

In the MLA(®) fibrinogen method for fibrinogen determination, 0.2 ml of Thromboplastin C were automatically added to 0.1 ml of the citrated plasma. The derived fibrinogen values and the prothrombin times were simultaneously and automatically determined by the MLA(®) instrument.

Linear regression analyses were performed on the fibrinogen values obtained by the four fibrinogen methods, and comparisons made using the Clauss method as the reference method.

Figure 7:
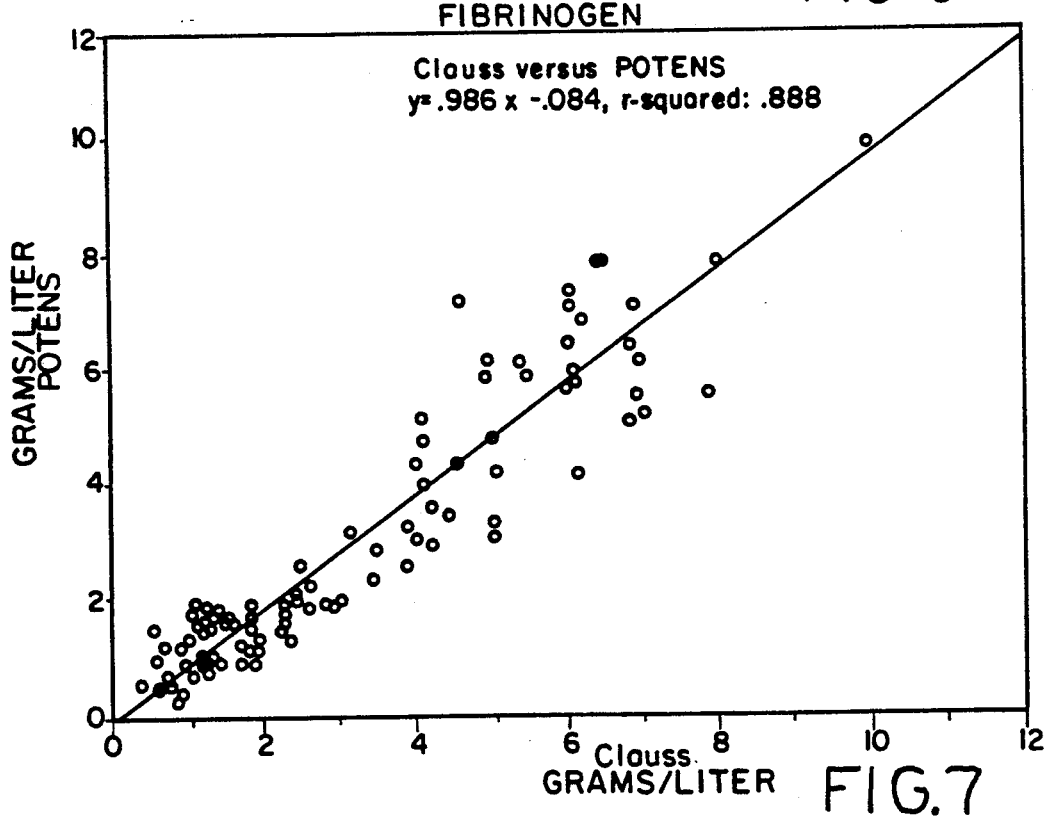
FIGS. 7, 8 and 9 depict the results of linear regression analyses performed on the fibrinogen values obtained by four methods, one of which is the "POTENS" method of the present invention.

FIG. 7 depicts the Clauss method fibrinogens vs. the potentiophotometer (POTENS) fibrinogens with $n=108$, $m=0.986$, $b=0.08$ Gm/L, $r^2=0.888$ and $r=0.942$, where n is the number of comparisons.

Figure 8:
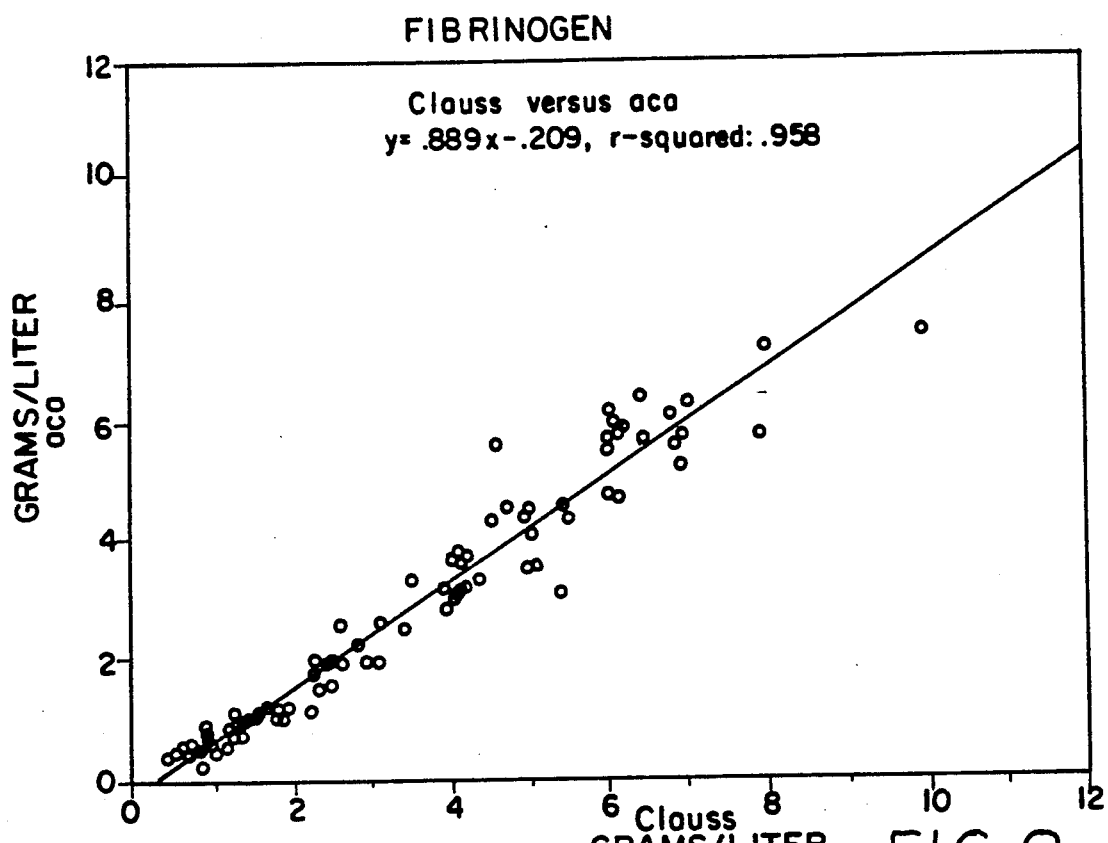

FIG. 8 depicts the Clauss method fibrinogens vs. the aca fibrinogens with $n=108$, $m=0.889$, $b=0.21$ Gm/L, $r^2=0.958$ and $r=0.979$.

Figure 9:
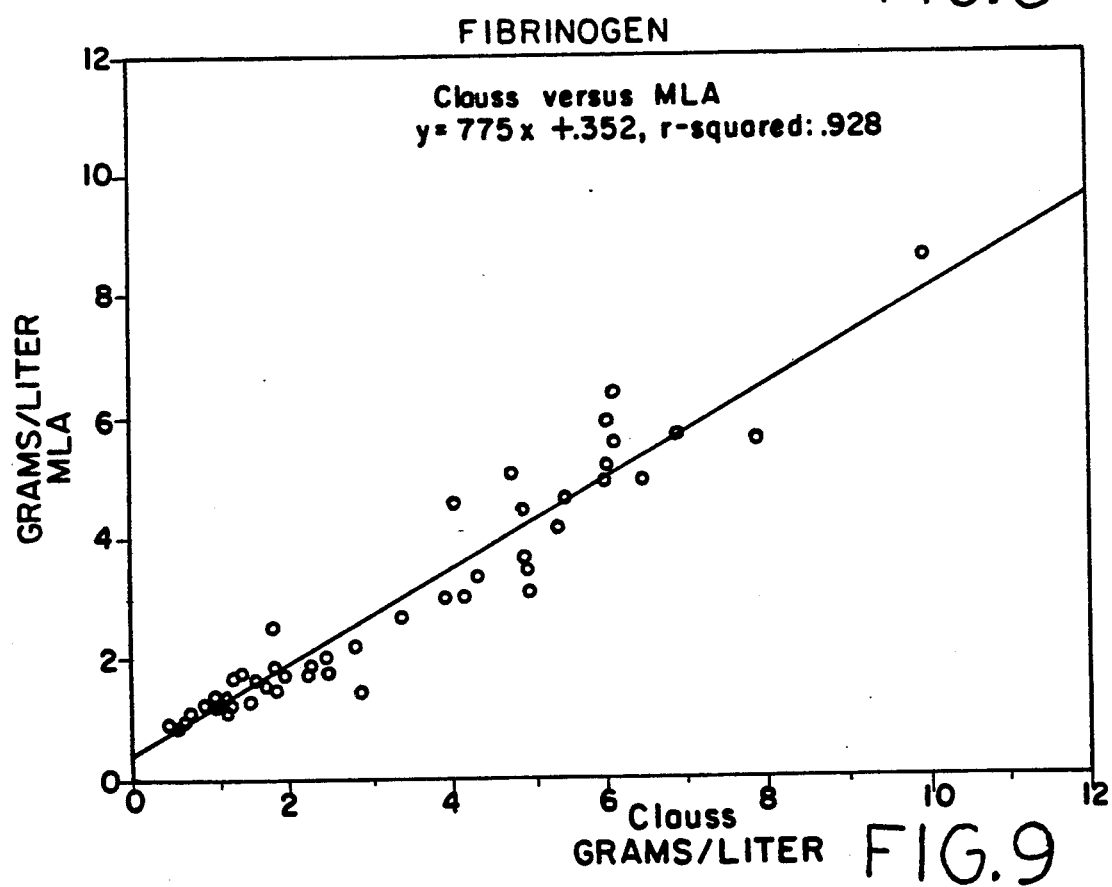
Figure 10:
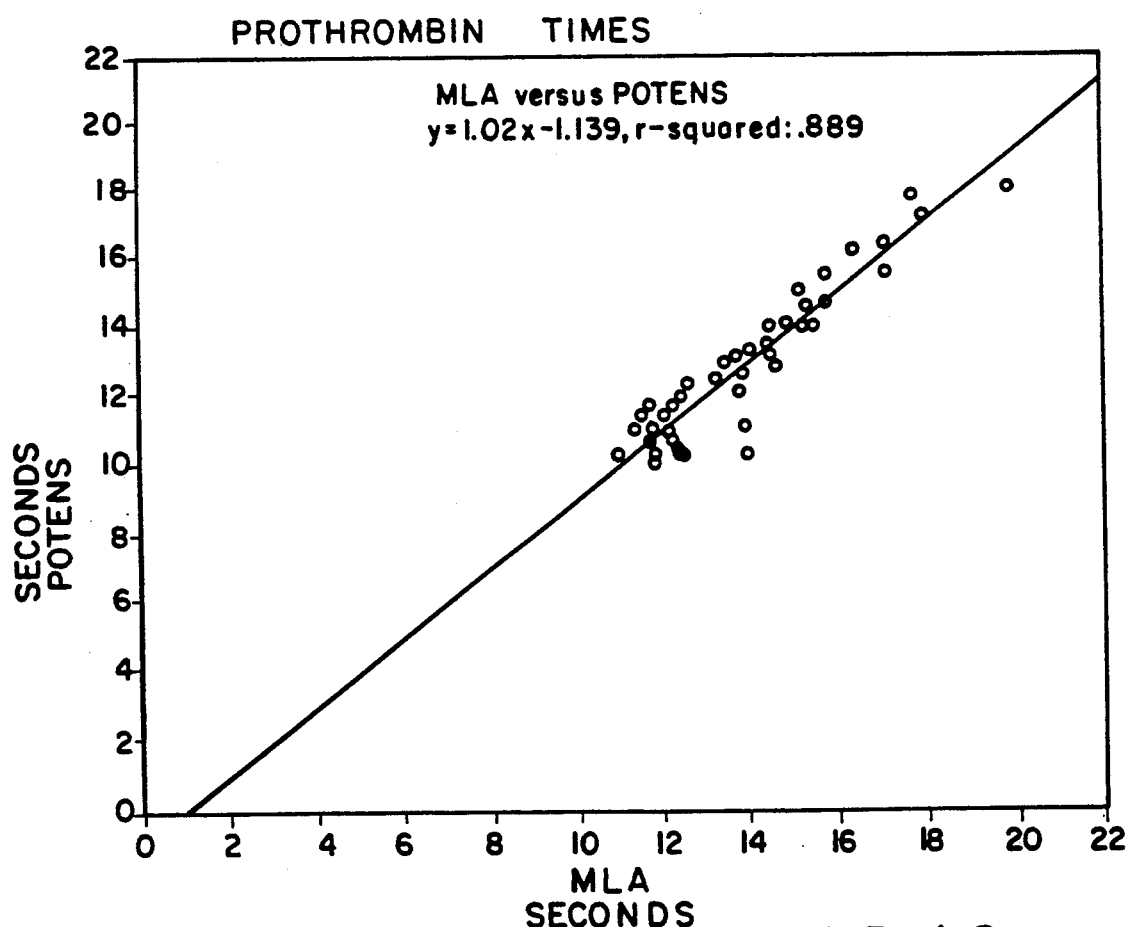
FIG. 10 is a comparison of 44 prothrombin times as calculated by the "POTENS" method of the present invention versus the method using the MLA Electra 900 C Analyzer.

FIG. 9 depicts the Clauss method fibrinogens vs. MLA(®) fibrinogens with $n=55$, $m=0.775$, $b=0.35$ Gm/L, $r^2=0.928$ and $r=0.963$.

The potentiophotometer, such as is shown in FIG. 1, is an instrument which embodies the electrical-analog solution to Beer's Law and whose output is expressed directly in the concentration of the substance being measured. In the present application, the value of this instrument in determining, automatically, the fibrinogen content of citrated human plasma while the prothrombin time is being performed is demonstrated. Losner, Volk, Jacobi and Newhouse, in an article published in Journal of Laboratory and Clinical Medicine, vol. 38 (1951) at pages 28-38, obtained the difference in (optical density) between clotted and unclotted plasma while performing the one-stage prothrombin time in a Coleman Spectrophotometer (Junior Model 6A). They multiplied this difference by 100 and called the result the clot density. They found that clot density was directly related to the fibrinogen concentration of the plasma and calculated the fibrinogens. Since the potentiophotometer output was calibrated directly in concentration units, no such manual calculations were necessary, and the fibrinogen values were obtained simultaneously with the one-stage prothrombin time.

Prior art methods and apparatus are disclosed in U.S. Pat. Nos. 3,307,392; 3,458,287; and 3,593,568. All of the cited references are incorporated herein by reference.

Several pieces of equipment, available commercially, have been mentioned in the forgoing specification. The duPont aca IV Analyzer is obtainable from E. I. duPont de Nemours and Co. (Inc.), Wilmington, Del. The MTA Electra 900 C Analyzer is obtainable from Baxter Healthcare Corp., Irvine, California, and as already mentioned, the ADALAB-PC TM is obtainable from Interactive Microware, Inc., State College, Pa. The MATRIX computer is obtainable from MATRIX, Woodland Hills, Calif.

Also mentioned in the forgoing specification are several products. The Owren's Veronal Buffer (pH 7.35) and the Thromboplastin C are both obtainable from Baxter Healthcare Corp., Miami, Fla.

We claim:

1. A method of measuring the optical density of a liquid sample comprising the steps of developing a series of analog electrical voltage signals having voltage amplitudes proportional to the optical density of the liquid sample, converting the developed analog voltage signals into a series of digital voltage value signals, separating the series of digital voltage value signals by a short, equal, selected time interval, recording the digital voltage signal values in successive lines in which each line consists of a selected equal number of digital voltage signal values totalling a selected time duration, terminating each recorded line when the number of recorded signals represents a selected time duration, injecting a coagulant into the liquid sample, thereby producing a change in the optical density of the liquid sample, said change producing a change in the amplitude of the electrical analog signals and a corresponding preselected minimum significant change in the recorded digital voltage signal values, allowing a preselected short time delay after said significant change of a preselected amount in the voltage value of the digital signals resulting from the injection and identifying the voltage value of the digital signal at the end of the delay as the baseline voltage value, thereafter comparing said identified baseline voltage value with succeeding recorded voltage values, observing a differential in the recorded digital signal values which exceeds a preselected minimum significant amount within a preselected time period Ta, identifying the voltage value of the digital signal at the beginning of said preselected time period Ta and denoting the beginning voltage value x, identifying the voltage value of the digital signal at the end of a preselected time period Tb following the time of recording voltage value x and denoting said ending voltage value as voltage value y, determining the differential between voltage value x and voltage value y and identifying the differential in voltage value between voltage value x and voltage value y as a delta voltage signal, using the forgoing steps to develop a delta voltage value signal for each of two calibrating samples having known values of optical density in units of mass, determining the relationship between the known values of optical density of the aforesaid two calibrating samples and the corresponding developed delta signals for said two calibrating samples, developing a delta voltage signal for a test sample having unknown optical density in units of mass using the steps indicated herein above, and determining the optical density of the test sample in units of mass from its developed delta voltage signal using the mean relationship between the two calibrating samples of known optical density in units of mass and the voltage values of the corresponding developed delta signals to derive from the delta voltage signal developed for the tested sample of unknown optical density the optical density of the unknown sample in units of mass.

2. A method according to claim 1 wherein the liquid sample is blood plasma.

3. A method according to claim 1 wherein the developed delta voltage signal is proportional to fibrinogen concentration in the sample.

4. A method according to claim 3 wherein a chart is used having delta voltage signals plotted along one axis and fibrinogen concentration in units of mass plotted along the other, wherein the delta voltage signals for each of two samples of known fibrinogen concentration are marked opposite the known value, in units of mass, of fibrinogen concentration, wherein a straight line is drawn between the two marks and projected linearly in both directions to form a calibration curve, and wherein the delta voltage signal developed for the sample of unknown fibrinogen concentration is marked on the calibration curve and the value in units of mass of fibrinogen concentration corresponding thereto is determined.

5. A method according to claim 1 wherein the recorded digital voltage signals are spaced apart by 0.05 seconds and wherein each line consists of twenty voltage signals totaling one second of time.

6. A method according to claim 1 wherein the coagulant which is injected into the sample is thromboplastin.

7. A method according to claim 1 wherein the preselected amount of the significant change in the voltage value of the recorded digital signals is plus or minus fifty voltage value units, thereby to exclude voltage changes due solely to turbulence.

8. A method according to claim 1 wherein the preselected short time delay after said significant change in the voltage value of the recorded digital signals is six seconds, to allow turbulence to subside.

9. A method according to claim 1 wherein the preselected amount of change in the digital voltage signal values within a preselected time period Ta is at least three voltage signal units and the preselected time period Ta within which this change occurs is one second.

10. A method according to claim 1 wherein the preselected time period Tb following the time of voltage value x to identify voltage value y is sixty seconds.

11. A method of measuring the fibrinogen concentration of a plasma sample comprising the steps of
developing an analog electrical voltage signal having amplitude proportional to the optical density of the sample,
converting the developed analog signal into a digital voltage value signal, representing the amplitude of the analog electrical signal,
separating successive digital voltage value signals by 0.05 seconds,
recording the digital voltage value signals in successive lines in which each line consists of twenty digital voltage values each spaced 0.05 seconds apart, said line totaling one second,
injecting thromboplastin into the plasma sample thereby to produce a change of at least plus or minus fifty voltage value units in the voltage values of the recorded digital signals,
allowing a short delay to permit the clearing up of any disturbance caused by the injection,
noting the voltage value of the recorded digital signal at the end of said short delay as the baseline voltage value,
thereafter comparing the aforesaid baseline voltage value with succeeding recorded voltage values,
observing a differential between the successive recorded voltage values which exceeds three voltage value units within a time period Ta of one second,
identifying the recorded voltage values of the digital signal at the beginning said one second time period Ta and denoting the beginning voltage value x,
identifying the voltage value of the digital signal at the end of a time period Tb sixty seconds following the time of recording voltage value x and denoting said voltage value y,
determining the differential in voltage value between voltage value x and voltage value y and identifying the differential in voltage value x to voltage value y as a delta voltage signal,
using the forgoing steps to develop a calibrating delta voltage value for each of two calibrating samples of known fibrinogen concentration,
marking said developed calibrating voltage values for said two calibrating samples on a chart in which delta voltage values are plotted along one axis and fibrinogen concentration in units of mass is plotted along the other,
drawing a straight line between said two calibrating delta voltage marks each of which is opposite a known value in mass units of fibrinogen concentration and projecting the line linearly in both directions to form a calibration curve,
developing a test delta voltage signal for a test sample of unknown fibrinogen concentration using steps indicated herein above,
marking the voltage values of the developed test delta voltage signal developed for the test sample of unknown fibrinogen concentration on the calibration curve and determining fibrinogen concentration in units of mass which corresponds thereto.

12. A method according to claim 11 wherein the time instant of said voltage value x is compared with the time instant of injection of thromboplastin to determine the prothrombin time.

13. A method according to claim 11 in which the analog electrical voltage signal is developed by transmitting a light beam through the plasma sample and sensing the variations in light passing therethrough to develop corresponding variations in the electrical signal produced.

14. Apparatus for measuring the optical density of a liquid sample comprising:
means including a light source, test tube, photocell, battery, and variable resistor for developing an analog electrical voltage signal having an amplitude proportional to the optical density of the liquid sample,
means including an A/D converter and digital recorder and computer for converting the developed analog signal into a series of digital voltage signal values each spaced apart by a short, equal, selected time interval,
means including the computer for recording the successive digital voltage value signals in successive lines in which each line consists of a selected equal number of digital voltage value signal totaling a selected time duration,
means for injecting a coagulant into the liquid sample, thereby producing a minimum significant change of at least a preselected amount in the voltage values of the recorded digital voltage value signal,
means including said computer for allowing a preselected short time delay after said significant change of a preselected amount in the voltage values of the recorded digital signal resulting from the injection and means for identifying the voltage value of the digital signal at the end of the delay,
means including said computer for thereafter comparing said identified voltage value with succeeding voltage values and for detecting a voltage change which exceeds a preselected amount of voltage change within a preselected time period Ta,
means including said computer for identifying the voltage value of the recorded digital signal at the beginning of said preselected time period Ta and denoting the beginning voltage value x, means including said computer for identifying the voltage value of the recorded digital signal at the end of a preselected time period Tb following the time of recording voltage value x and denoting the ending voltage value voltage value y, means including said computer for determining the differential in voltage value between voltage value x and voltage value y and identifying the differential in voltage value between voltage value x and voltage value y as a delta voltage signal, means for using the foregoing steps to develop a delta voltage signal for each of two calibrating samples having known values of optical density, in units of mass, a chart showing a calibration curve which passes through said delta voltage signals of said two calibrating samples, and means including said light source, test tube, photocell, battery and variable resistor for developing a delta voltage signal for a test sample having unknown value of optical density, in units of mass, using the steps indicated hereinabove, and whereby the relationship between the two calibrating samples of known optical density in units of mass and the voltage values of the developed delta signals corresponding thereto is used to derive from the delta voltage signal developed for the test sample of unknown optical density the value of optical density in units of mass of the unknown sample.

15. Apparatus according to claim 14 wherein the liquid sample is blood plasma.

16. Apparatus according to claim 14 wherein the developed delta voltage signal is proportional to fibrinogen concentration in the sample.

17. Apparatus according to claim 16 wherein a chart is used having delta voltage signals in units of mass plotted along one axis and fibrinogen concentration plotted along the other, wherein the delta voltage signals for each of two calibrating samples of known fibrinogen concentration are marked opposite the known value of fibrinogen concentration, wherein a straight line is drawn between the two marks and projected linearly in both directions to form a calibration curve, and wherein the delta voltage signal developed for the test sample of unknown fibrinogen concentration is marked on the calibration curve and the value in units of mass of fibrinogen concentration corresponding thereto is determined.

18. Apparatus according to claim 14 wherein the recorded digital voltage signals are spaced apart by 0.05 seconds and wherein each line consists of twenty voltage signals totaling one second of time.

19. Apparatus according to claim 14 wherein the coagulant which is injected into the sample is thromboplastin.

20. Apparatus according to claim 14 wherein the preselected amount of the significant change in the voltage value of the recorded digital signals is plus or minus fifty voltage value units.

21. Apparatus according to claim 14 wherein the preselected short time delay after said significant change in the voltage value of the recorded digital signals is six seconds.

22. Apparatus according to claim 14 wherein the preselected amount of voltage change in the digital-signal value within a preselected time period is at least three voltage value units and the preselected time period within which this voltage change occurs is one second.

23. Apparatus according to claim 14 wherein the preselected time period following the time of voltage value x to identify voltage value y is sixty seconds.

24. Means for measuring the fibrinogen concentration of a plasma sample comprising:

means including a light source, test tube, photocell, battery and variable resistor for developing an analog electrical voltage signal proportional to the optical density of the sample with an amplitude, means including an A/D converter and digital recorder and computer for converting the developed analog signal into a series of digital voltage signals representing the value of the amplitude of the analog electrical signal each spaced apart by 0.05 seconds, means including the computer for recording the digital voltage signals in successive lines in which each line consists of twenty digital voltage signals each spaced 0.05 seconds apart, said line totaling one second, means for injecting thromboplastin into the plasma sample thereby to produce a change of at least fifty voltage value units in the voltage values of the recorded digital signals, means including the computer for allowing a short delay to permit the clearing up of any disturbance caused by the injection, means including the computer for identifying the voltage value of the digital signal at the end of the short delay, means including a print out chart with arrays of numbers for thereafter comparing the aforesaid voltage value with succeeding voltage values and means including said arrays of numbers for identifying a change in voltage which exceeds three voltage value units within a time period Ta of one second, means including said arrays of numbers for identifying the voltage values of the digital voltage signal at the beginning of the one second time period Ta and denoting the beginning voltage value x, means including said arrays of numbers for identifying the voltage value of the digital signal at the end of a time period Tb sixty seconds following voltage value x and denoting it voltage value y, means including said arrays of numbers for determining the differential in voltage value between voltage value x and voltage value y and identifying the differential between voltage value x and voltage value y as a delta voltage signal, means including said arrays of numbers for using the forgoing steps to develop a delta voltage signal for each of two calibrating samples having known fibrinogen concentration, means including a chart for marking the two last named delta voltage signals in which delta voltage signals are plotted along one axis and fibrinogen concentration in units of mass is plotted along the other, a straight line drawn between the two delta marks each of which is opposite a known value of fibrinogen concentration, said line projecting linearly in both directions to form a calibration curve, means including said light source, test tube, photocell, battery and variable resistor for developing a delta voltage signal for a test sample of unknown fibrinogen concentration using steps indicated herein above, said chart having marks thereon indicating the values of the delta voltage signal developed for the sample of unknown fibrinogen concentration on the calibration curve and said chart having said calibration curve for determining the value of fibrinogen concentration which corresponds thereto.

25. Apparatus according to claim 24, including means for comparing the time instant of voltage value x with the time instant of injection of thromboplastin to determine the prothrombin time.

26. Apparatus according to claim 24, including means for developing an analog signal by transmitting a light beam through the plasma sample and receiving the transmitted light on a light sensitive voltaic cell.

* * * * *